(12) United States Patent
Hawtin

(10) Patent No.: US 7,109,246 B1
(45) Date of Patent: Sep. 19, 2006

(54) PHARMACEUTICAL COMPOSITIONS COMPRISING AN AMPHOTERIC SURFACTANT AN ALKOXYLATED CETYL ALCOHOL AND A POLAR DRUG

(75) Inventor: Brian Hawtin, Derbyshire (GB)

(73) Assignee: Hewlett Healthcare Ltd, Derby (GB)

( * ) Notice: Subject to any disclaimer, the term of this patent is extended or adjusted under 35 U.S.C. 154(b) by 0 days.

(21) Appl. No.: 09/701,140

(22) PCT Filed: May 20, 1999

(86) PCT No.: PCT/GB99/01600

§ 371 (c)(1),
(2), (4) Date: Nov. 21, 2000

(87) PCT Pub. No.: WO99/60997

PCT Pub. Date: Dec. 2, 1999

(30) Foreign Application Priority Data

May 22, 1998 (GB) ................................. 9810949.9

(51) Int. Cl.
*A61K 31/395* (2006.01)
(52) U.S. Cl. ........................ 514/861; 514/937; 514/715
(58) Field of Classification Search ............. 424/78.03; 514/861, 863, 887, 939, 945
See application file for complete search history.

(56) References Cited

U.S. PATENT DOCUMENTS

| | | | | |
|---|---|---|---|---|
| 4,868,192 A | * | 9/1989 | Totten et al. ................ | 514/291 |
| 4,883,792 A | * | 11/1989 | Timmins et al. ............. | 514/169 |
| 5,000,936 A | * | 3/1991 | Chibret ........................ | 424/43 |
| 5,100,908 A | * | 3/1992 | Murata et al. .............. | 514/396 |
| 5,152,914 A | * | 10/1992 | Forster et al. .............. | 252/174 |
| 5,190,917 A | * | 3/1993 | Lezdey et al. ................. | 514/12 |
| 5,562,642 A | * | 10/1996 | Smith et al. ................. | 604/289 |
| 5,696,110 A | * | 12/1997 | Bourrain et al. ............. | 514/211 |
| 5,837,274 A | * | 11/1998 | Shick et al. ................. | 424/406 |
| 5,888,478 A | * | 3/1999 | Maurin ......................... | 424/45 |
| 5,939,085 A | * | 8/1999 | Jacobs et al. ............... | 424/401 |
| 5,959,137 A | * | 9/1999 | Collin et al. ................ | 560/160 |
| 6,071,541 A | * | 6/2000 | Murad ......................... | 424/616 |
| 6,143,310 A | * | 11/2000 | Sang et al. .................. | 424/401 |
| 6,150,400 A | * | 11/2000 | Nyirjesy et al. ............. | 514/456 |
| 6,150,403 A | * | 11/2000 | Biedermann et al. .......... | 424/7 |
| 6,165,479 A | * | 12/2000 | Wheeler ...................... | 424/400 |
| 6,177,092 B1 | * | 1/2001 | Lentini et al. .............. | 424/401 |
| 6,207,694 B1 | * | 3/2001 | Murad ......................... | 514/396 |
| 6,231,844 B1 | * | 5/2001 | Nambu ........................ | 424/70.31 |

FOREIGN PATENT DOCUMENTS

| | | |
|---|---|---|
| EP | 0 189 861 | 8/1986 |
| EP | 0 208 009 | 1/1987 |
| GB | 1 445 437 | 8/1976 |
| GB | 1 475 503 | 6/1977 |
| GB | 1 537 047 | 12/1978 |
| GB | 2 202 145 B | 9/1988 |
| JP | 0157172 | 6/1997 |
| JP | 9157161 | 6/1997 |

OTHER PUBLICATIONS

Dener et al. Abstract of WO 98/04537, published Feb. 5, 1998.*
Handbook of Cosmetic Science and Technology, 1st Edition, 1993. Elsevier Science Publishers LTD, p. 67.*
Haider SA. Treatment of atopic eczema in children-. A clinical trial of10% sodium cromoglycate ointment. BMJ (1977); 1570-1572.
Ariyanayagam et al (1985) Br J Dermatol 112(3), 343-348.
Merck Index twelfth edition Budvari Ed (1996) excerpts relevant to documents 3 and 4.
Thirumoothy T, Greaves MW. Disodiumcromoglycate ointment in atopic eczema. BMJ (1978); 500-501.
Croner S, et al. Sodium cromoglycate ointment in atopic eczema during childhood. Opuscula Medica (1981) 26(2): 49-50.
Zachafiae H, Testrup-Pederson K, Thulin H, Thormann J, Herlin T, Cramers M, Jensen J, Kragballe K, Afzelius H, Overgaard Petersen H. Experimentaltreatment in atopic dermatitis: immunologial background & preliminary results. Acta Dermatovener (Stockholm) Suppl. (1980) 92:121-12.
Haider SA.. Treatment of atopic dermatitis in children.—Use of topical sodium cromoglycate. From The Mast Cell; Its role in Health and Desease. Eds. Pepys and Edwards (1979); Pitman Medical. 570-6.
Pearce CA, Greaves MW, Plummer VM. Yamamoto S. Effect of sodium cromoglycate on antigen evoked histamine release in human skin. Clin Exp Immunol (1974) 17:437-440.
Clegg LS, Church MK, Holgate ST. Histamine secretion from human skin slices induced by anti-lgE and artificial secretagogues and the effects of sodium cromoglycate and salbutamol. Clin Allergy(1985)15(4):321-328.
Okayama Y, Benyon RC, Rees PH, Lowman MA, Hillier K, Church MK. Inhibition profiles of sodium cromoglycate and nedocromil sodium on mediator release from mast cells of human skin, lung, tonsil, adenoid and intestine. Clin Exp Allergy (1992)22(3): 410-409.
Crossman DC, Dashwood NR Taylor GW, Wellings R, Fuller RW. Sodium cromoglycate: evidence of tachykinin antagonist activity in the human skin. J Appl Physiol (1993) 75(1): 167-172.
Walsh LJ. Ultraviolet B irradiation of skin induces mast cell degranulation and release of tumour necrosis factor. Immunology and Cell Biology (1995) 73: 226-233.
Page C. Sodium cromoglycate, a tachykinin antagonist. Lancet (1994) 343:70.
Edwards AM, Norffs AA. Cromoglycate and asthma. Lancet (1994) 343:426.
Ting S, Zweiman B, Lavker R. Cromolyn does not modulate human allergic skin reaction in vivo, J Allergy Clin Immunol (1983) 71(1 Pt 1): 12-17.

(Continued)

Primary Examiner—Sreeni Padmanabhan
Assistant Examiner—Gina C. Yu
(74) Attorney, Agent, or Firm—Haugen Law Firm PLLP

(57) ABSTRACT

A formulation, for example an oil-in-water emulsion, comprising an amphoteric surfactant, alkoxylated cetyl alcohol and a polar drug. The drug may be sodium cromoglycate or nedocromil sodium. The formulation may be useful in the treatment of skin disease such as atopic dermatitis.

9 Claims, 1 Drawing Sheet

OTHER PUBLICATIONS

Figure 1:
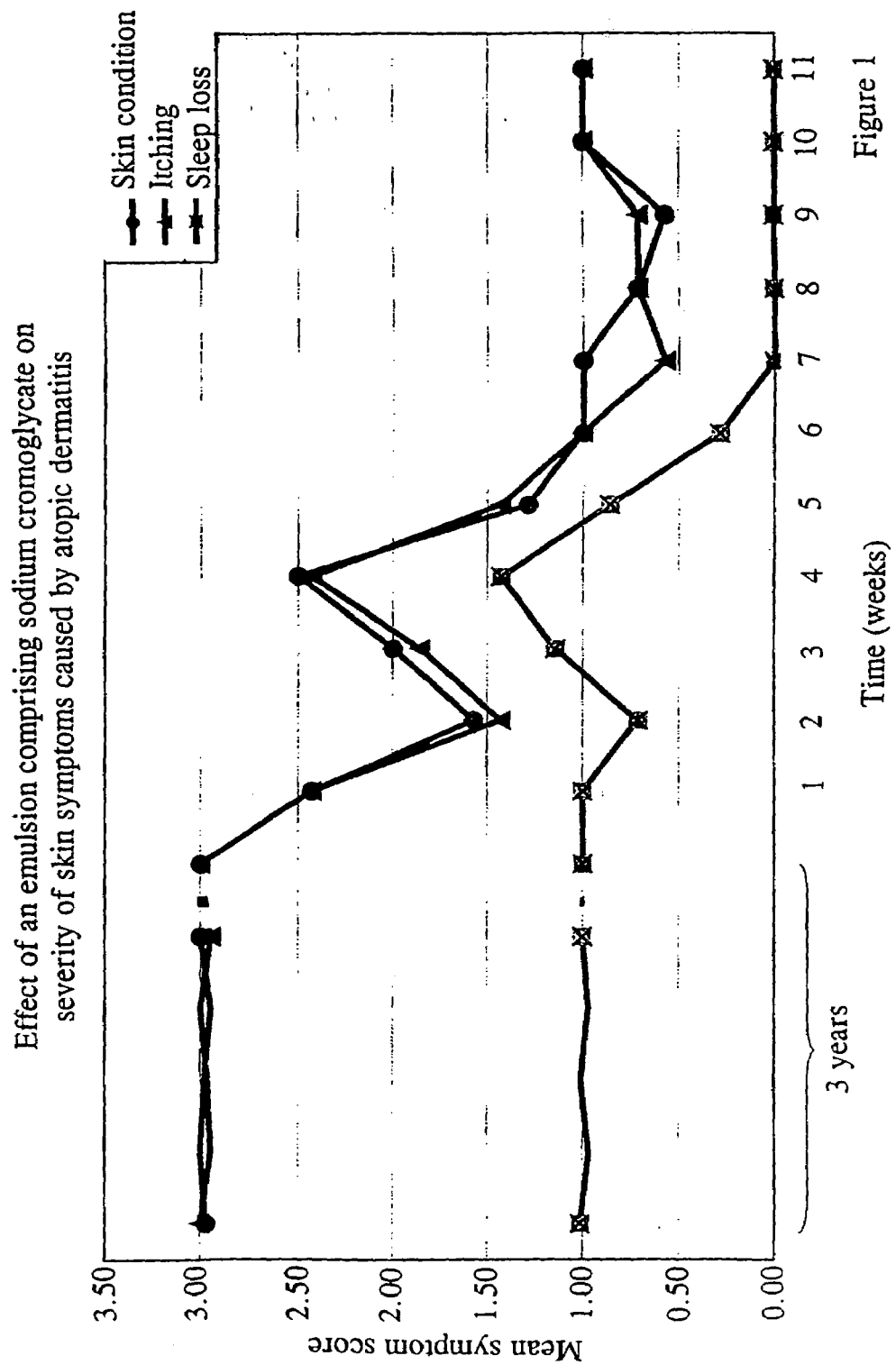

Van Bever HP, Stevens WJ. The effect of local application of disodium cromoglycate (DSCG) solution on skin prick tests. J Allergy Clin Immunol (1991)1:226A.

Gronneberg R, Zetterstrom O. Effect of local application of disodium cromoglycate on anti-1gE induced early and late skin response in humans. Clin Allergy (1985)15(2): 167-171.

Kimata H, Igarashi M. Inhibition of human allergic skin reactions in vivo by pretreatment with cromolyn (disodium cromoglycate). Allergy (1990)45:393-395.

Phillips TJ, Kanj LF, Washek D, Lew R. Topical cromolyn can modify human allergic skin reactions. Allergy (1996)51(3) 198-199.

Kjellman N-I M and Gustafsson IM. Topical sodium cromoglycate in atopic dermatitis. Allergy (1986)44(6): 423-428.

Pike MG and Atherton DJ. Failure of a new topical sodium cromo-glycate formulation to improve atopic dermatitis. Eur J Ped (1988)148(2): 170.

Neale MG, Brown K, Hodder Rw, Auty RM. The pharmacokinetics of sodium cromoglycate in man after intravenous and inhalation administration. Br J Clin Pharmac (1986)22:373-382.

Kimata H, Igarashi MIE. Topical cromolyn (disodium cromoglycate) solution in the treatment of young children with atopic dermatitis. Clin Exp Allergy (1990)20:281-283.

Kimata H, Hiratsuka S. Efect of topical sodium cromoglycate solu-tionon atopic dermatitis: combined treatment of sodium cromoglycate solution with the oral antiallergic medication, oxatomide. Eur J Pediatr (1994)153:66-71.

Hiratsuka S, Yoshida A, Ishioka C, Kimata H. Enhancement of in vitro spontaneous IgE production by topical steroids in patients with atopic dermatitis. J Allergy Clin Immunol (1996)98:107-113.

Loh RKS, Jabara HH, Geha RS. Disodium cromoglycate inhibits Sμ-Se deletional switch recombination and IgEsynthesis in Human B cells. J Exp Med (1994)180(2):663-671.

Wu CY, , Sarfati M, Heusser C, Poumeir S, Rubio-Trujillo M, Deles-pesse G. Glucocorticoids increase the synthesis of immunoglobulin E by interleukin-4 stimulated human lymphocytes. J Clin Invest (1991)87:870-877.

McHenry PM, Willimas HC, Bingham EA. Managementof atopic eczema. BMJ (1995)310:843-847.

Atopic dermatitis and cromolyn. Clin Exp Allergy (1990)20:243-244.

European Task Force on Atopic Dermatitis. Severity scoring of atopic dermatitis: The SCORAD index. Dermatology (1993) 186:23-31.

Ishikura et al (1987) Drug Design & Delivery 1, 285-295.

Van Bever & Stevens (1989) Eur J Pediatr 149, 74.

Cox JSG et al. Disodium Cromoglycate (Intal. Advances in Drug Research) (1970): 5,115-196.

Moore C et al. Topical sodium cromoglycate in the treatment of moderate to sever atopic dermatitis. Ann Allergy Asthma Immunol (1998)81, 452-458.

Church MK et al. Cromolyn sodium and nedocromil sodium: mast cell stabilizers, neuromodulators or anti-immflamatory drugs? In Kaliner MA et al (eds). Asthma: its pathology and treatment. New York: Marcel Dekker, (1991)561-593.

Jackson DM et al. The effects of sodium cromoglycate on histamine aerosol-induced reflex bronchoconstriction in the anaesthetized dog. Br J Pharmac (1977)61,257-262.

Dixon M et al. The action of sodium cromoglycate on "C" fibre endingsin the dog lung. Br J Pharmacol(1980)70,11-13.

Richard IM et al. Alternative modes of action of sodium cromoglycate. Agents Actions (1986)18(3/4), 294-300.

Collier JG et al. Evidence for an effect of sodium cromoglycate on sensory nerves in man. Br J Clin Pharmacol (1983)16,639-643.

* cited by examiner

PHARMACEUTICAL COMPOSITIONS COMPRISING AN AMPHOTERIC SURFACTANT AN ALKOXYLATED CETYL ALCOHOL AND A POLAR DRUG

The present invention concerns formulations for the topical administration of drugs.

Sodium cromoglycate (termed cromolyn sodium in the USA and variously also known as disodium cromoglycate or disodium 5,5'-[(2-hydroxytrimethylene)dioxy]bis-[4-oxo-4H-1-benzopyran-2-carboxylate]) is known to have beneficial effects in the treatment of atopic conditions, particularly asthma. Some positive results have been obtained in clinical trials addressing its efficacy with regard to atopic dermatitis (also known as eczema or atopic eczema) and associated skin disorders.

Atopic dermatitis is an inflammatory skin disorder, affecting up to 10% of the paediatric population. It is characterised by extreme itching, a chronic relapsing course and specific distribution around the body. There is usually a family history of allergy and the condition starts in early infancy.

Typical treatment regimes are to use simple emollients or topical corticosteroids. Long-term use of topical corticosteroids may have undesirable side effects, particularly in children.

Topical preparations containing sodium cromoglycate have been attempted (ointments, aqueous solutions and creams) but their clinical effect has been disappointing. This may be due to low bioavailability of sodium cromoglycate in the dermis, which may arise from poor penetration of the skin. Sodium cromoglycate is likely to have poor skin penetration properties arising from its extremely polar nature.

In the early 1980's it was shown that the formulations used by Haider (refs 1 to 5) were unlikely to achieve good skin penetration and Fisons developed a 4% oil in water cream formulation which had better skin penetration in model experiments. This was used in a clinical trial programme of which 3 trials were published (18, 19, 20). Only one of these trials by Arianayagam et al (20) showed positive effects. In this study, a significant effect was seen on the total eczema score after 9 and 12 weeks of treatment. It was also shown that the greatest effect was seen in those subjects with a Total Serum IgE of <500 U/ml. However the skin penetration of this formulation was relatively poor with the calculated bioavailability of the applied dose ranging from 0.01% to 2.75%. This compares to a bioavailability of 10–15% when the drug is administered by inhalation in the treatment of asthma (21).

In 1990 Kimata and Igarishi (22) published a 4 week, placebo-controlled, double-blind trial of 1% aqueous solution of sodium cromoglycate. After application of the aqueous solution the skin was occluded with white soft paraffin. All patients had moderate to severe atopic dermatitis with Total Serum IgE levels ranging from 100 to 8600 U/ml. The sodium cromoglycate treated group exhibited significant benefits on the skin after one week's treatment and on the itch and sleep disturbance after two weeks. Further studies were published as Kimata and Hiratsuka (23) and Hiratsuka et al (24).

The results of topical sodium cromoglycate in atopic dermatitis are extremely variable. This may be result of the different formulations, or concentrations used or the patient population selected or a combination of all three. The concentrations used have ranged from 1% to 10% and the formulations include aqueous solution, creams and ointments. The most positive results have been seen in relatively young children (Range 6 months to 7 years) who are strongly atopic (Serum IgE>2SD from normal).

It is also probable that adequate skin penetration of the drug is an essential pre-requisite of clinical efficacy in order for the drug to attach to the receptors responsible for the allergic inflammation and itch. Sodium cromoglycate is an extremely polar compound and may have poor penetration of skin and mucous membranes. Little is known about its absorption through the skin in patients apart from the formulation used by Ariyanayagam et al which gave relatively low levels of absorption. Hiratsuka et al were unable to detect any sodium cromoglycate in the blood using a radioimmunoassay after applying an aqueous solution of the drug but it would seem unlikely that the drug was not absorbed in view of the demonstrated effects on B cell activity and on cytokine release. Sodium cromoglycate is not metabolised and is rapidly removed from the blood and the levels may have been below the level of detection. Urinary levels over time are probably a better measure of bioavailability. Haider encouraged his patients to rub the ointment into the skin (personal communication) which may have increased the penetration.

At the publication of the first Japanese trial the journal carried an editorial (28) which stated "Given the frequent adverse effects of therapeutic alternatives, it certainly seems worth pursuing the potential benefits of topical cromolyn solution. . . . An effective, safe new drug to be used in the treatment of this troublesome disease would be very welcome."

There is therefore a long-felt interest in and need for the development of an acceptable vehicle that allows adequate skin penetration of sodium cromoglycate, for use in the treatment of atopic dermatitis. So far a suitable vehicle has not been found, despite much interest in the area. Such a vehicle may be useful in a product that may fit as a maintenance treatment, particularly in children, between simple emollients and topical corticosteroids which at present are the mainstay treatment for this condition (27).

Ariyanayagam et al (20), for example, report that Bodor et al (1980; *Int J Pharmaceut* 7, 63) have produced a series of lipophilic pro-drugs in an attempt to improve the bioavailability of sodium cromoglycate.

As discussed above, oil-in-water emulsions comprising sodium cromoglycate (or the related chromone nedocromil sodium) are known. Some of these emulsions further comprise anionic surfactants. None comprise amphoteric surfactants, nor is the use of amphoteric surfactants suggested. None comprise alkoxylated cetyl alcohol, a substance used as a water soluble surface active emollient in personal care products.

GB 2 202 145 B, for example, describes several topical formulations of nedocromil sodium (sodium 9-ethyl-6,9-dihydro-4,6-dioxo-10-propyl-4H-pyrano(3,2-g)quinoline-2,8-dicarboxylate), including an oil-in-water emulsion.

Ishikura et al (1987) *Drug Design & Delivery* 1, 285–295 describes the use of amphoteric surfactants in improving percutaneous uptake of diltiazem hydrochloride (used as an example of a cationic water soluble drug) from water-soluble films. Whilst investigation of uptake of sodium cromoglycate (used as an example of an anionic water soluble drug) was also reported in the paper, the effect of the amphoteric surfactants on sodium cromoglycate uptake was not suggested or tested.

The present work surprisingly shows that a composition, for example an oil-in-water emulsion, comprising an amphoteric surfactant, alkoxylated cetyl alcohol and a polar drug, for example sodium cromoglycate, may be formed.

The composition has been found to be stable, and an effective amount of the drug may penetrate the skin of a patient when the formulation is applied topically. The composition may be useful in the treatment of skin disease such as atopic dermatitis.

The composition of the present invention avoids anionic or cationic substances and provides a stable formulation, for example a stable emulsion, comprising the polar substance sodium cromoglycate. The polarity of sodium cromoglycate may limit the stability of known emulsions. The amphoteric surfactant may assist in overcoming this problem and may also assist the skin penetration of the sodium cromoglycate. Use of alkoxylated cetyl alcohol and an amphoteric surfactant in combination may be particularly beneficial in producing a stable and effective formulation, for example an emulsion, comprising a polar drug, for example sodium cromoglycate or nedocromil sodium.

Thus, a first aspect of the invention is a composition comprising an amphoteric surfactant, an alkoxylated cetyl alcohol and a polar drug.

The composition may comprise an aqueous phase and an oil phase. It may be an emulsion or may be used in the manufacture of an emulsion. It may, for example, form or be comprised in the aqueous phase of an emulsion. It is preferred that the emulsion is an oil-in-water emulsion but it will be appreciated that the emulsion may alternatively be a water-in-oil emulsion.

A "polar drug" is a compound which may be used as an active ingredient in a medicament that is water-soluble and ionises on solution in distilled water at 25° C. A "water-soluble" compound may be dissolved in distilled water at 25° C. at a ratio of compound to water (weight to volume, or volume to volume if the compound is a liquid) of at least 1 to 10000, 1 to 1000, 1 to 100, 1 to 30, 1 to 10, 1 to 1 or 1 to less than 1. It is preferred that the polar drug comprises an anionic polar drug, for example a chromone, such as nedocromil sodium or sodium cromoglycate. Most preferably, the drug comprises sodium cromoglycate.

Other examples of polar drugs that may be suitable include polar anti-inflammatory or antirheumatic agents, for example ibuprofen; antibacterial agents, for example agents that may be useful in the treatment of acne (for example clindomycin sodium phosphate or tetracycline); a hormone, for example an oestrogen; a polar analgesic, for example fentanyl; a polar motion-sickness treatment molecule, for example scopolamine or hyoscine; an antihypertensive, for example clonidine; a vasodilator or coronary vasodilator, for example nitroglycerine; or nicotine.

Further preferred examples of suitable polar drugs include a polar corticosteroid formulation, for example a salt of an esterified corticosteroid, for example a salt of a phosphate or succinate ester. Such polar formulations may be soluble in water and are the form commonly used for injections or solutions. Suitable salts of esters of corticosteroids include betamethasone sodium phosphate, dexamethasone sodium phosphate, hydrocortisone sodium phosphate, hydrocortisone sodium succinate, methylprednisolone sodium succinate and prednisolone sodium succinate.

The drug may be useful in treating skin disease or may be a drug that is useful when administered transdermally.

The drug, for example sodium cromoglycate, may constitute from 0.01 to 20% w/v, preferably 0.1 to 20% w/v, still more preferably 1 to 10% w/v, yet more preferably about 7.5% w/v, most preferably about 4% w/v of the composition, for example the emulsion. When the polar drug comprises a corticosteroid, the corticosteroid may preferably constitute 0.01 to 10% w/v, preferably from 0.1 to 10% w/v, most preferably about 0.25 or 0.5% w/v of the composition, for example the emulsion.

It will be appreciated that it is preferred that the above proportions are present in a composition of the invention that is a formulation, for example an emulsion, as may be administered to a patient, for example applied to the skin of the patient. It will further be appreciated that a composition of the invention may be useful in preparing a formulation, for example an emulsion, suitable for administration to a patient, for example application to the skin of a patient; for example, the composition may form the aqueous phase of the emulsion, or it may be a concentrate used in the preparation of the aqueous phase of the emulsion, as known to those skilled in the art. Thus, it will be appreciated that in these examples of compositions of the invention, it may be preferred that the proportion of the composition that is the polar drug may be from about 1.5 to about 10 times greater than that given above.

It will be appreciated that the composition, for example emulsion, may comprise more than one polar drug. Thus, for example, a preferred composition, for example emulsion, of the invention may comprise a chromone, such as nedocromil sodium or sodium cromoglycate, and a corticosteroid. The corticosteroid may constitute 0.01 to 10% w/v, preferably from 0.1 to 10% w/v, most preferably about 0.25 or 0.5% w/v of the emulsion or other formulation as administered to a patient, as above. Preferences for the corticosteroid are as given above; most preferably it is betamethasone sodium phosphate.

It is preferred that an emulsion is stable. By this is meant that separation of the oil and water phases is not detectable by visual inspection after a period of at least one day, preferably one week, still more preferably one month, yet more preferably six months or a year after manufacture when stored at 15° C. to 30° C. Storage may be at, for example, 22° C.

It will be appreciated that the composition, for example emulsion, may be presented as a lotion or as a foam, as known to those skilled in the art.

The term "amphoteric surfactant" is well known to those skilled in the art. Such surfactants (which may also be known as ampholytic surfactants) possess at least one anionic group and at least one cationic group, and can therefore have anionic, non-ionic or cationic properties depending on the pH. If the isoelectric point of the molecule occurs at pH7, the molecule is said to be balanced. Amphoteric surfactants may have detergent and disinfectant properties. Balanced amphoteric surfactants may be particularly non-irritant to the eyes and skin.

Amphoteric surfactants are characterised by their ability to move between having a cationic or anionic charge dependent upon pH. In the presence of highly polar molecules such as sodium cromoglycate in a weak acid solution (for example, pH6), these surfactants may be compatible with the changes to charges around the molecule as it disassociates or associates (in the case of sodium cromoglycate, between the positive sodium and negative cromoglycate elements), providing a consistent medium for surface wetting and skin penetration.

It will be appreciated that the composition, for example emulsion, should not contain ingredients that may cause irritation to the skin, even on prolonged use. Compounds to which sensitisation may occur should be avoided. Thus, balanced amphoteric surfactants may be preferred.

The pH of skin is about 4.5. In order to avoid irritation to the skin, a pH that is slightly acidic, ie to the acid side of neutral, is preferred, for example a pH between about 4.5 and about 7.0. For example, the emulsion may be manufactured to a pH of 6.0, for example using sodium dihydrogen orthophosphate as the buffer agent.

Examples of amphoteric surfactants include aminocarboxylic acids, aminopropionic acid derivatives, imidazoline derivatives, dodicin, pendecamaine or long-chain betaines, Nikkol AM101® (2-alkyl-N-carboxymethyl-N-hydroxyethyl imidazolinium betaine), Nikkol AM310® (lauryldimethylaminoacetic acid betaine), Nissan Anon #300 (12 w/v % alkyldiaminoethylglycine hydrochloride, 3 w/v % alkyldiethylene-triaminoglycole hydrochloride; Inui Shouji Co, ADG), C31G (a mixture of alkyl betaines and alkyl amine oxides), N-tetradecyl-N,N-dimethyl-3-ammonio-1-propanesulfonate) or cocamidopropyl betaine. Any of these may be used, but cocamidopropyl betaine may not be preferred as instances of allergy to this compound, when used in shampoo, have been reported (De Groot et al (1995) *Contact Dermatitis* 33(6), 419–422).

It will be appreciated that an amphoteric surfactant may be supplied (as an "amphoteric surfactant" or amphoteric surfactant preparation) packaged or compounded with other substances by the manufacturer, and that references to an amphoteric surfactant encompass an amphoteric surfactant alone and a preparation supplied as an amphoteric surfactant by the manufacturer. It is preferred that the amphoteric surfactant is a carboxylated imidazoline derivative. It is particularly preferred that the amphoteric surfactant comprises disodium coacoamphodiacetate. It is still more preferred that the disodium coacoamphodiacetate is packaged or compounded with lauryl sulphate and hexylene glycol, as is known to those skilled in the art.

It is particularly preferred that the amphoteric surfactant preparation has the following composition:

disodium coacoamphodiacetate 5 to 30% w/w, for example 14% w/w sodium lauryl sulphate 2 to 20% w/w, for example 12.5% w/w hexylene glycol 3 to 20% w/w, for example 7% w/w sodium chloride 0.25 to 15% w/w, for example 3.9% w/w lauryl alcohol 0.1 to 5% w/w, for example 1.0% w/w hydrochloric acid 0.1 to 5% w/w, for example 1.0% w/w sodium sulphate 0.025 to 2.5% w/w, for example 0.25% w/w formadehyde 0.003 to 1% w/w, for example 0.03% w/w water to 100% w/w Such a preparation may be Miracare 2MCA/E™, supplied by Rhône-Poulenc Chemicals, Poleacre Lane, Woodely, Stockport, Cheshire SK6 1PQ. This preparation is very well tolerated on skin. As a strong surfactant, it may rapidly "wet-out" the skin, penetrating the skin's natural oily barrier and assisting the trans-dermal passage of the sodium cromoglycate or other polar drug. The action of breaking down the oils in the skin also enhances skin hydration from the water present in the emulsion.

The amphoteric surfactant may be incorporated in the water phase of an oil-in-water emulsion that is a preferred embodiment of the invention. This may assist skin penetration by the polar drug, for example sodium cromoglycate, and may hold the emulsion stable. In the absence of an amphoteric surfactant, the emulsion may break down over a period of 24 hours into two phases, ie the oils will separate and float to the surface. The amphoteric surfactant may constitute from 0.05 to 20% weight to volume (w/v) of the emulsion, preferably 0.1% to 10% w/v, still more preferably 1 to 5% w/v, most preferably about 2% w/v of the emulsion. It will be appreciated that the above proportions may refer to an amphoteric surfactant alone or to an amphoteric surfactant preparation, as described above, for example to a preparation comprising disodium coacoamphodiacetate, laurylsulphate and hexylene glycol, such as Miracare 2MCA/E™. Preferably, the proportions refer to an amphoteric surfactant preparation. The amphoteric surfactant component may constitute from 0.007 to 2.8% w/v, 0.014 to 1.4% w/v, 0.14 to 0.7% w/v or most preferably 0.28% w/v of the emulsion.

It will be appreciated that when determining the percentage weight to volume of an ingredient of the composition, for example emulsion, or a solute to solvent, the weight in grams of the ingredient is compared with the volume in milliliters (ml) of the prepared composition, for example emulsion.

The term alkoxylated cetyl alcohol encompasses polypropoxylated cetyl alcohol, the chemical description given for Procetyl AWS™ in Gardner's Chemical Synonyms and Trade Names, ninth edition. Alkoxylated cetyl alcohol may be obtained from Croda Chemicals Ltd., Cowick Hall, Snaith, Goole, North Humberside, DN14 9AA. It is marketed as "Procetyl AWS™". The alkoxylated cetyl alcohol may be useful for its water soluble surface active emollient properties. It may also act as an emulsifying and solubilising agent and imparts a silky feel to the skin.

The alkoxylated cetyl alcohol may constitute from 0.1 to 20% w/v, preferably from 0.1 to 10% w/v, still more preferably from 0.5 to 4% w/v of the emulsion and most preferably 1% w/v of the emulsion.

It will be appreciated that it is preferred that the above proportions may be present in a composition of the invention that is a formulation (that is not necessarily an emulsion) that may be administered to a patient, for example applied to the skin of the patient. It will further be appreciated that a composition of the invention may be useful in preparing a formulation, for example an emulsion, suitable for administration to a patient, for example application to the skin of a patient; for example, the composition may form the aqueous phase of the emulsion, or it may be a concentrate used in the preparation of the aqueous phase of the emulsion, as known to those skilled in the art. Thus, it will be appreciated that in these examples of compositions of the invention, it may be preferred that the proportion of the composition that is the alkoxylated cetyl alcohol or amphoteric surfactant may be from about 1.5 to about 10 times greater than those given above.

It will be appreciated that the critical ingredients of the formulation, for example the emulsion, are the amphoteric surfactant, alkoxylated cetyl alcohol and the drug component (for example, sodium cromoglycate). Further ingredients may include water and an oil phase. Suitable components of the oil phase will be known to those skilled in the art, and the following description is not limiting.

It is preferred that the components of an emulsion are chosen such that the emulsion is acceptable to a patient using it. For example, it should not be too greasy. It is preferred that the emulsion has an appropriate viscosity for spreading smoothly over the skin with low friction over areas of broken or sensitive skin. Thus, the emulsion may not have the appearance of a solid at 22° C. or at 37° C. It is preferred that the emulsion may have a viscosity of between about 10, 20, 100, 200 or preferably 400 to 20,000 centipoise or mPas at 22° C. or 37° C. It is further preferred that the emulsion has a viscosity between about 1400 to 2600 centipoise, preferably between about 2000 to 2600 centipoise, when measured at a maximum shear rate of 210 sec$^{-1}$ and between about 2300 to 3800 centipoise, preferably between about 3000 to 3800 centipoise, when measured at maximum shear rate of 125 sec$^{-1}$. Methods of measuring viscosity are well known to those skilled in the art and are described, for example, in Chapter 22 of *Remington's Pharmaceutical Sciences* 15th Ed, Mac Publishing. For comparison, the viscosity of olive oil is about 138 mPas at 10° C. and about 36 mPas at 40° C. The emulsion may appear as a watery lotion, which may be applied via a bottle dispenser. More preferably, the emulsion may appear as a cream which at 20° C. remains in an open container when the container is inverted, and may be dispensed using a hand pump attached to a bottle, such as may be used for dispensing liquid hand soap. Reference 18 sets out some desirable characteristics of preparations for treating atopic dermatitis.

The emulsion may appear as a foam which may be applied via a pressurised dispenser. When presented as a foam, it may be desirable for the emulsion to be more dilute with regard to excipients and the same or more concentrated with regard to the polar drug than an emulsion presented as a lotion, as described above. This may reduce the viscosity of the emulsion and aid the dispensing of the foam.

The oil phase may comprise liquid paraffins, white soft paraffin, glycerol monostearate, non-ionic emulsifying wax or a lipophilic non-ionic surfactant (for example sorbitan tristearate), benzyl alcohol and/or isopropyl myristate. These terms are well known to those skilled in the art. Isopropyl myristate is an example of an emollient. Glycerol monostearate is an example of an emulsifying agent and may also act as an emollient. Benzyl alcohol is an example of a preservative and a mild local anaesthetic. The non-ionic emulsifying wax may be Polawax NF™ (a blend of higher fatty alcohols and polyoxyethylene sorbitan fatty acid ester, in particular a blend of cetostearyl alcohol and sorbitan tristearate). Non-ionic emulsifying wax may be useful in the preparation of emulsions comprising polar substances. A lipophilic non-ionic surfactant, for example sorbitan tristearate, may be used as an alternative to or in addition to a non-ionic emulsifying wax. Liquid paraffins and isopropyl myristate may act as emollients and form an occlusive film on the skin as water dries away from the emulsion. This film may assist in keeping the skin hydrated from the water applied in the emulsion.

Liquid paraffins may provide from 0.1% to 30% w/v, preferably 1% to 20% w/v, still more preferably 5% to 15% w/v and most preferably about 10% w/v of the emulsion.

White soft paraffin may provide from 0.1% to 30% w/v, preferably 1% to 20% w/v, still more preferably 2% to 15% w/v and most preferably about 5% w/v of the emulsion.

Glycerol monostearate may provide from 0.1 to 10% w/v, preferably 0.5% to 5% w/v, still more preferably 1% to 3% w/v, most preferably 2% w/v of the emulsion.

The nonionic emulsifying wax, for example Polawax NF™, or lipophilic non-ionic surfactant, for example sorbitan tristearate, may provide from 0.1 to 15% w/v, preferably 0.5 to 5% w/v, still more preferably about 2% w/v of the emulsion. It is preferred that a lipophilic non-ionic surfactant, for example sorbitan tristearate, provides from 0.5 to 5% w/v of the emulsion or that the nonionic emulsifying wax, for example Polawax NF™, provides from 2 to 5% w/v. It will be appreciated that if the nonionic emulsifying wax, for example Polawax NF™ provides more than about 5% of the emulsion that the resulting emulsion may be too viscous to spread easily on the skin.

Isopropyl myristate may provide from 0.1 to 10% w/v, preferably 0.5 to 5% w/v, still more preferably about 2% w/v of the emulsion.

Benzyl alcohol may provide from 0.001 to 5% w/v, preferably from 0.01 to 1.0% w/v, still more preferably about 0.2% w/v of the emulsion.

The aqueous phase comprises water and the drug. It may further comprise one or more preservatives. Disodium edetate (EDTA) and Triclosan (5-chloro-2(2,4-dichlorophenoxy)phenol) are suitable compounds with preservative properties. The drug may be in solution in the aqueous phase. EDTA may also contribute to the stability of the formulation by forming complexes with any heavy metal ions. Triclosan may have a residual antibacterial effect on the skin and may assist with limiting any damage at an eczema site arising from bacterial colonisation. The anti-infective effect of the preservative, for example Triclosan and/or benzyl alcohol may also serve to prevent potential infection from the prolonged rubbing process involved during administration.

Disodium edetate may provide from 0.001 to 5% w/v, preferably 0.01 to 1% w/v, still more preferably about 1% w/v of the emulsion.

Triclosan (5-chloro-2(2,4-dichlorophenoxy)phenol) may provide from 0.001% to 5% w/v, preferably 0.01% to 1.0% w/v, still more preferably about 0.2% w/v of the emulsion.

The emulsion may consist essentially of the components listed below, preferably in substantially the quantities listed below. It is preferred that the drug is sodium cromoglycate or nedocromil sodium, most preferably sodium cromoglycate.

sorbitan tristearate or non-ionic emulsifying wax (Polawax NF) 2.0% glycerol monostearate 2.0% light liquid paraffin 10.0% white soft paraffin 5.0% isopropyl myristate 3.0% drug 7.5% disodium edetate 0.1% amphoteric surfactant 2.0% (for example disodium coacamphodiacetate, which may be compounded with lauryl sulphate and hexylene glycol, for example Miracare 2MCA/E™)

alkoxylated cetyl alcohol 1.0% triclosan 0.2% benzyl alcohol 0.2% purified water 67.0%

Sorbitan tristearate may be obtained under the name Crill 35™ from Croda Chemicals Limited, Cowick Hall, Snaith, Goole, North Humberside DN14 9AA. Polawax NF™ may also be obtained from Croda Chemicals Limited. It is preferred that Polawax NF™ is used in preference to sorbitan tristearate (Crill 35™).

Alternatively, the drug, for example sodium cromoglycate, may be present at 4.0% w/v (or 2% or 8% w/v, for example) and purified water at 70.5% (or 72.5% or 66.5%, for example).

The pH of the emulsion may be adjusted to 6.0 using sodium dihydrogen orthophosphate.

The emulsion may appear as a cream or a watery lotion. The lotion may be rubbed into the affected skin for about 3 to 5 minutes. During this process, the lotion may first go white, then clear and then disappear into the skin, leaving a protective barrier that may help to stop the skin drying out.

An emulsion of the invention may be prepared by methods well known to those skilled in the art. For example, it may be prepared by heating the oils to about 70° C., then adding them steadily to the water phase (also at or about 70° C.) with good stirring, and then allowing the emulsion to cool.

Once an emulsion has been formed, further water may be added with stirring if desired, for example in preparing a formulation suitable for delivery as a foam. A suitable formulation for delivery as a foam may be prepared by diluting an emulsion essentially as described above by the addition of one part water to two parts emulsion. It will be appreciated that if an emulsion is to be diluted before application to the skin that it may be preferred that the concentration of the drug, for example sodium cromoglycate, in the emulsion may be calculated such that the desired concentration, for example 4%, is achieved in the diluted formulation. It will be appreciated that it is preferred that the emulsion is formed with the composition that it is intended to apply to the skin, for example with the additional water referred to above ab initio so that dilution is not necessary.

A suitable formulation for delivery as a foam may consist essentially of the components listed below, preferably in substantially the quantities listed below. It is preferred that the drug is sodium cromoglycate or nedocromil sodium, most preferably sodium cromoglycate.

sorbitan tristearate or non-ionic emulsifying wax (Polawax NF™) 1.3% light liquid paraffin 6.6% white soft paraffin 3.3% isopropyl myristate 2.0% drug 4% disodium edetate 0.66% amphoteric surfactant 1.3% (for example disodium coacamphodiacetate, which may be compounded with lauryl sulphate and hexylene glycol, for example Miracare 2MCA/E™)

alkoxylated cetyl alcohol 0.66% triclosan 0.13% benzyl alcohol 0.13% purified water to 100% (about 78.6%)

A further aspect of the invention is a stable oil-in-water emulsion comprising sodium cromoglycate, wherein when the emulsion is applied to skin an amount of sodium cromoglycate penetrates the skin that is sufficient to produce a demonstrable effect in the treatment of atopic dermatitis/eczema.

The amount of sodium cromoglycate that penetrates skin may be measured by techniques well known to those skilled in the art, some of which are mentioned above. Methods include in vitro measurements on skin biopsies (which may be human or animal, preferably rodent, still more preferably hairless rat skin) or in vivo measurements. For example, the presence of sodium cromoglycate in plasma or urine following topical application to a human or experimental animal (for example rat or rabbit) may be measured. Such measurements are described in Ishikura et al (1987) cited above, and Ariyanayagam et al (20). Sodium cromoglycate may be quantified by techniques of analytical chemistry, for example high performance liquid chromatography (HPLC).

Effectiveness of the emulsion may be measured in animal models of atopic dermatitis, or in clinical trials on humans, for example as described in Examples 3 to 6. Preferably it is measured in humans.

Patients having atopic dermatitis may be diagnosed by criteria known to the skilled person. For example, patients may be diagnosed by a general medical practitioner recognising the effect of atopic eczema on the surface of the skin. Several sets of criteria for diagnosis have been proposed in order to assist in achieving consistency between studies of the condition ((29) and Williams et al (1996) B J Dermatol 135, 12–17). The criteria discussed in Williams et al include: a history of an itchy skin plus three or more of: (i) a history of rash in the skin creases (folds of elbows, behind the knees, fronts of ankles or around the neck); (ii) a personal history of asthma or hay fever; (iii) a history of generally dry skin in the last year; (iv) onset under the age of 2; and (v) visible flexural dermatitis as defined by a photographic protocol.

The criteria by which an effect on atopic dermatitis may be judged are set out in reference 29.

It may be necessary to select patients on the basis of the level of circulating IgE. Suitable IgE tests include an in vitro total IgE test and an in vitro specific IgE test, for example the UniCAP Total (or Specific) IgE tests sold by Pharmacia & Upjohn, which use the Allergen InnumunoCAPS™ as the allergen reagent.

It may be desirable or necessary for patients to be screened according to their IgE levels before treatment with sodium cromoglycate is undertaken.

More specifically, patients with total serum IgE levels below 150 iu/ml may be less likely to respond to the treatment. It is preferred that the patient is a child between the ages of 6 months and 10 years with atopic dermatitis.

A further aspect of the invention is a method of treatment of a skin disease or condition wherein a drug is applied to the skin of an individual affected by the disease or condition in or with a formulation comprising alkoxylated cetyl alcohol and an amphoteric surfactant. The drug may be present in a formulation comprising the alkoxylated cetyl alcohol or it may be applied to skin before, after or at the same time as the said formulation, which may or may not comprise further amounts of the same or a different drug.

It is preferred that the drug is a polar drug, as discussed above. The formulation may aid penetration of the drug, particularly a polar drug, through the skin by altering the nature of the barrier presented by the skin, as described above. It will however be appreciated that the drug may be a non-polar drug, for example a non-polar drug useful in the treatment of a skin disease or condition, for example a non-polar form of a corticosteroid, as found, for example, in creams prepared for topical application, for example in Betnovate™, Eumovate™ or Aureocort™ cream, as described further below. It is preferred that a non-polar drug, for example a non-polar form of a corticosteroid is applied to the skin before, after, or at the same time as the said formulation, preferably substantially immediately before or substantially immediately after the said formulation, most preferably, before or immediately before the said formulation. The formulation may form a film over the surface of the skin which is beneficial, for example in retaining moisture.

Preferences for the said formulation are as for the compositions of the invention but it will be appreciated that the formulation may not comprise a polar drug if a drug is applied separately to the skin.

It is preferred that the formulation comprises sodium cromoglycate or nedocromil sodium and/or a corticosteroid, for example a polar form of a corticosteroid such as a salt of an esterified corticosteroid, as described above. The drug may alternatively be an antibacterial agent, for example an antibacterial agent that may be useful in treating acne, as described above.

A further aspect of the invention is the use of an alkoxylated cetyl alcohol and an amphoteric surfactant in the manufacture of a medicament for the treatment of a skin disease or condition. A drug, preferably a polar drug may further be used in the manufacture of the said medicament.

In the following aspects of the invention, it is preferred that the composition or emulsion of the invention comprises sodium cromoglycate or nedocromil sodium and/or a corticosteroid, for example a polar form of a corticosteroid such as a salt of an esterified corticosteroid, as described above.

A further aspect of the invention is a method of treatment of a skin disease or condition comprising applying a composition or emulsion of the invention to the skin of an individual affected by the disease or condition.

A still further aspect of the invention is the use of a composition or emulsion of the invention in the manufacture of a medicament for the treatment of a skin disease or condition.

It is preferred that the skin disease or condition is a disease of humans, but may also be one that affects other mammals, for example cats, dogs or horses. The disease or condition may be any in which skin mast cells and/or delayed (cellular) hypersensitivity reactions and/or inflammation is thought to be involved.

It is preferred that the disease or condition is atopic dermatitis or eczema, but it may also be contact sensitivity, psoriasis, drug sensitivity reactions, apthous ulcers, Behcet's syndrome, pemphigus, urticaria, urticaria pigmentosa, pyroderma gangrenosum, chronic skin ulcers, ulcers associated with Crohn's disease, burns, insect stings/bites, herpetic infections, systemic sclerosis (systemic scleroderma), morphoea (circumscribed or localised scleroderma) and dermal nodular fibrosis.

The skin disease or condition may be being, may have been or may be further treated by application of a corticosteroid. It may be beneficial to treat a patient, particularly a patient with atopic dermatitis or eczema, with a combination of a cromone and a corticosteroid. The therapeutic effects of a cromone such as sodium cromoglycate and corticosteroids may not be wholly interchangeable, as described in Altounyan & Howell (1969) "Treatment of asthma with disodium cromoglycate (FPL 670, "Intal")" *Respiration* 26(suppl), 131–140 and in Altounyan (1979) *Proceedings of Allergy* (Pitman Medical). A minimum dose of corticosteroids may be necessary below which sodium cromoglycate is without clinical effect. Further, corticosteroids alone, even in high dosage, may not achieve the same therapeutic response as a lower dose of corticosteroid together with sodium cromoglycate. Haider (5) suggests that sodium cromoglycate may exert a corticosteroid-sparing effect in atopic eczema or that there may be a synergism between the two.

The cromone and corticosteroid may be presented in the same formulation or in separate formulations. The cromone and corticosteroid may be presented as separate formulations for topical application. Either or both formulations (if appropriate) may be a composition, for example an emulsion, of the invention. As described in Examples 3 and 4, a formulation comprising a corticosteroid may be applied before or after (preferably before) a formulation of the invention comprising a cromone for example sodium cromoglycate. The corticosteroid may be in a polar or a non-polar form; preferably it is in a non-polar form if it is not presented in a composition of the invention. Suitable formulations comprising a non-polar corticosteroid include the proprietary formulations Betnovate RD™ (bethamethasone valerate, ready diluted), Aureocort™ (triamcinolone acetonide and chlortetracycline hydrochloride (an antibiotic)), and Eumovate™ (clobetasone butyrate). A 1% hydrocortisone preparation may also be used.

It will be appreciated that bethamethasone valerate and triamcinolone acetonide may be considered to be potent corticosteroids, and clobetasone butyrate may be considered to be a moderately potent corticosteroid, as classified, for example, in Martindale, the Extra Pharmacopoeia, 31$^{st}$ Edition. Hydrocortisone may be considered to be a mild corticosteroid. It will be appreciated that the corticosteroid preparation used in combination with an emulsion of the invention comprising a cromone may be chosen depending upon the severity of the symptoms to be treated. A stronger (for example, moderately potent or potent) corticosteroid may be used at the start of combination therapy, which may be replaced by a weaker (for example a mild or moderately potent) corticosteroid as the symptoms are brought under control. Thus, if the symptoms are exacerbated, for example as the result of the patient contracting a cold, then a stronger corticosteroid may be used until the symptoms are diminished, whereupon a weaker corticosteroid may be used, as described in Example 3.

Symptoms that may be assessed include skin itching, sleep loss and skin condition, for example redness and the presence of sores or scabs.

The compositions or emulsions of the invention comprising sodium cromoglycate or nedocromil sodium, may also be useful in the treatment of sunburn or in sunscreen preparations. They may also be useful in cosmetic preparations, for example anti-ageing creams.

A further aspect of the invention is a method of treatment of a patient in need of a polar drug comprising applying a composition or emulsion of the invention comprising the said polar drug to the skin of the said patient. The polar drug may be or may comprise, for example, a polar anti-inflammatory or antirheumatic agent, for example ibuprofen; an antibacterial agent, for example an agent that may be useful in the treatment of acne (for example clindomycin sodium phosphate or tetracycline); a hormone, for example an oestrogen; a polar analgesic, for example fentanyl; a polar motion-sickness treatment molecule, for example scopolamine or hyoscine; an antihypertensive, for example clonidine; a vasodilator or coronary vasodilator, for example nitroglycerine; or nicotine.

A still further aspect is the use of a composition or emulsion of the invention in a method of treating a patient in need of the said polar drug.

The patient in need of a polar drug may be, for example, a patient with arthritis that is in need of a polar anti-inflammatory or antirheumatic agent, for example ibuprofen. Alternatively, the patient in need of a polar drug may be a patient with acne that is in need of a polar antibacterial drug, for example clindomycin sodium phosphate or tetracycline. The patient in need of a polar drug may be a patient in need of nicotine, for example a patient who is attempting to give up cigarette smoking. Polar drugs that may be suitable for treating particular conditions when administered transdermally will be known to those skilled in the art.

The composition or emulsion may be packaged or presented in any convenient way. For example, it may be packaged in a tube, tub, bottle or pressurised aerosol, using techniques well known to those skilled in the art and as set out in reference works such as *Remington's Pharmaceutical Sciences* 15th Ed, Mac Publishing. It is preferred that it is packaged in such a way as to minimise contact of the unused composition or emulsion with the environment, in order to minimise contamination of the composition or emulsion both before and after the container is opened. It is particularly preferred that the composition or emulsion is packaged in a pressurised aerosol container or in a plastic dispenser bottle. For example, an emulsion comprising sodium cromoglycate at either 4% or 8% w/v may be packaged in a plastic dispenser bottle, which may contain one month's supply (between about 150 and 300 ml).

It will be appreciated that the emulsion may have the appearance of a cream or a lotion, or of a foam.

The composition or emulsion may be applied topically to affected areas or prophylactically to unaffected areas. The composition or emulsion may be applied as directed by a physician. For example, the affected area may be rubbed, for example for at least about 5 minutes, to apply the composition or emulsion, in order to encourage absorption of the drug. The composition or emulsion may be applied once or twice a day, or at greater or lesser intervals, depending upon the needs of the patient, as determined by the patient or a physician. As described above, a composition or emulsion of the invention comprising a cromone may be applied after a formulation comprising a corticosteroid.

The invention will now be described by reference to the following, non-limiting, figures and examples.

FIG. 1: Mean symptom score following treatment with corticosteroids and an emulsion comprising sodium cromoglycate. Details of the treatment are described in Example 3.

EXAMPLE 1

Preparation of an Oil-in-Water Emulsion Comprising Sodium Cromoglycate

The following substances are combined to form an emulsion. The percentages refer to percentages w/v of the final emulsion.

Group A sorbitan tristearate or Polawax NF™ 2.0% glycerol monostearate 2.0% light liquid paraffin 10.0% white soft paraffin 5.0% isopropyl myristate 3.0% benzyl alcohol 0.2%

Group B sodium cromoglycate 7.5% disodium edetate 0.1% amphoteric surfactant 2.0% (for example disodium coacamphodiacetate, which may be compounded with lauryl sulphate and hexylene glycol, for example Miracare 2MCA/E™)

alkoxylated cetyl alcohol 1.0% triclosan 0.2% purified water 67.0%

The emulsion is prepared by heating the oils (compounds in group A) to about 70° C., then adding them steadily to the water phase (compounds in Group B; also at or about 70° C.) with good stirring, and then allowing the emulsion to cool. The batch size may be between about 10 liters and about 500 liters or more. The emulsion is prepared using a high shear homogeniser, as known to those skilled in the art. The mixture is stirred as the ingredients are mixed and stirring should continue until the mixture cools to room temperature. Overstirring of the mixture does not appear to be detrimental. If the mixture is not stirred sufficiently, the emulsion may not form, or if it does form, may be unstable and may crack ie return to the component oil and water phases.

EXAMPLE 2

Clinical Trial of Efficacy of the Emulsion Comprising Sodium Cromoglycate in the Treatment of Atopic Dermatitis Patients for the clinical trial may be selected on the basis of a diagnosis of atopic dermatitis, or on the basis of a diagnosis of atopic dermatitis with total Serum IgE greater than 200 units/ml.

Patients may be of any age and may be children, for example aged 6 months to 5 years. Patients may have any level of severity of diagnosed atopic dermatitis, or may be selected on the basis of severity, for example those with mild or moderate disease only, those with active disease only (ie not disease in remission), those with severe disease only.

A suitable trial population may, for example, be children aged between 6 months and 5 years with total Serum IgE greater than 200 units/ml.

The clinical trial methodology will follow that recommended by the European Task Force on Atopic Dermatitis (29).

EXAMPLE 3

Effect of a Composition of the Invention on Severity of Skin Symptoms Caused by Atopic Dermatitis The composition of the invention had the following composition:

Polawax NF™ 2.0% glycerol monostearate BP 2.0% light liquid paraffin BP 10.0% white soft paraffin BP 5.0% isopropyl myristate BPC 3.0% sodium cromoglycate 4.0% disodium edetate BP 0.1%

Miranol™ 2.0%

Procetyl AWS™ triclosan 0.2% benzyl alcohol BP 0.2%

Deionised water 70.5%

The pH is adjusted to 6.0 using sodium dihydrogen orthophosphate.

Background Information

Patient TR aged 3.5 years has suffered from severe atopic dermatitis since he was 3–5 weeks old. Treatment before using the composition of the invention was topical steroid applied two times per day. This had been applied for 3 years and was not effective.

Treatment with the Composition of the Invention

The patient began by applying Aureocort™ (triamcinolone acetonide [a potent corticosteroid] and chlortetracycline hydrochloride) and then the composition of the invention on top.

After 3 days Aureocort™ was replaced with a milder steroid (Eumovate™; clobetasone butyrate [a moderately potent corticosteroid]) and the symptoms continued to improve. On day 13 the order was changed so The composition of the invention was applied first and then Eumovate™, but this was not found to be as effective and the skin became red and sore. On day 19 the application order was returned to Eumovate™ followed by the composition of the invention.

On day 25 the patient became ill with a cold that exacerbated his skin symptoms and on day 26 stopped using the composition of the invention for three days as it was causing a feeling of heat. Aureocort™ was used on its own for 2 days and then with the composition of the invention for a further 6 days until the skin was almost clear, when the use of Eumovate™ followed by the composition of the invention was recommenced.

Another cold on day 35 affected the patient's asthma but did not worsen the eczema or stop the patient using the composition of the invention.

8 weeks after the start of treatment the skin was almost clear and there were hardly any sores or scabs on the patient's body.

Recording of Results

The condition of the skin, itching and sleep lost due to itching were recorded every day and measured on a scale of 0 to 3 where 3=severe, 2 moderate, 1 slight and 0=none.

Results

The results of the treatment have been plotted in the graph shown in FIG. 1. It shows the mean score per week for each symptom.

The symptoms improved immediately and after 3 days, the patient could be moved on to a milder topical corticosteroid treatment. In week 2, the deterioration may be due to applying the corticosteroid treatment after the composition of the invention. This may have been further exacerbated in week 3 by a cold. In weeks 4 and 5 the condition was brought under control by a combination of the composition of the invention and a stronger corticosteroid and in week 6 the patient returned to the milder corticosteroid in combination with the composition of the invention.

The symptoms continued to improve and the patient's skin became almost clear and very smooth, such that by week 7 there were hardly any sores or scabs on the patient's body.

Further measurements were made of the area affected, the corticosteroid cream usage and the mother's assessment of the patient's condition. The first two showed a significant reduction, and the mother considered there to be a "fabulous improvement".

Seven other named patients between the ages of 3 and 25 were treated with the composition of the invention. Initially, some patients were given a 7.5% foam-based formulation. This proved effective. A burning sensation was noticed by some patients, especially on areas of broken skin. Later, patients were given a 4% solution presented as a formulation of the invention, in particular the formulation described above. This has improved the skin condition in all patients. A burning sensation was noticed in some cases. Patients successfully controlled using the composition of the invention are able to reduce or eliminate steroid use, and 5 out of 7 patients are continuing to use the composition of the invention on a routine basis.

EXAMPLE 4

Tolerability and Absorption Studies

The studies are to assess the safety and tolerability of the composition of the invention described in Example 3, and to measure the systemic absorption of sodium cromoglycate. The formulations tested are those with 0%, 2%, 4% or 8% sodium cromoglycate.

The studies are double-blind, randomised, placebo-controlled, ascending dose studies.

Each subject receives only one of the above medication strengths which is applied topically twice daily for seven days to a pre-defined area on the forearms and abdomen. Thirty-six healthy volunteers are examined, at least four of which must be male and at least four of which must be female.

The subjects are dosed in three groups of 12 subjects each (nine to receive formulations comprising sodium cromoglycate and three to receive the formulation with no sodium cromoglycate). Seven days of treatment may be sufficient to reach steady state with this formulation.

The study formulation is administered by spreading evenly over the following areas: the volar aspects of both forearms and the abdomen. The study formulation is spread by the subject using two fingers of each hand. Sufficient formulation is used to just cover the defined area. The subject does not wear gloves. The container of study formulation for each subject is weighed before dosing. The site where the formulation is administered is left uncovered for one hour and is then covered up. The container is reweighed following dosing in order to determine the mass of study formulation remaining. The dosing procedure is repeated at 12 hour intervals. The drug is applied to the same three areas of skin on each occasion for seven days (a total of 14 doses administered).

The drug administration sites are assessed before and after application for Draize scale assessments and skin symptoms, including itch.

Urine is collected for assay of the 24 hours cumulative urinary excretion of unchanged cromoglycate ($Ae_{0-24}$) on the seventh day of drug treatment. Although systemic absorption is best assessed in terms of plasma or serum drug concentrations, a sensitive assay for measurement of the anticipated low drug levels of sodium cromoglycate is not generally available. Urinary recovery is therefore used as a means of assessing drug absorption.

Urine samples are assayed for unchanged cromoglycate by liquid chromatography/mass spectrometry (LC/MS). The limit of quantification is 0.05 mg/L.

Assessment of adverse events, skin related symptoms and Draize scale assessments are measured. Subjects are questioned regarding itch and other skin-related symptoms.

It is expected that the formulation is found to be well-tolerated and that absorption is below the level seen with inhaled sodium cromoglycate. Sodium cromoglycate has a reputation for being a very safe drug in clinical practice and is well documented. However, some adverse effects do occur. These are generally reported as transient, the main ones being headache, dizziness, local irritation of the target organ and an unpleasant taste in the mouth.

There are also some other effects that are dependent on the route of administration. Eye drops occasionally cause burning and stinging. Oral administration may cause nausea, skin rash and joint pain. Intra-nasal administration may cause epistaxis. For a topical formulation applied to the skin, irritation of the skin may cause a burning or stinging sensation.

Currently, the largest doses of sodium cromoglycate administered in clinical use are for asthma (20 mg inhaled up to 8 times daily; maximum administered dose of 160 mg, with 13–24 mg absorbed, given the bioavailability of 8–15%) and food allergy (up to 40 mg/kg/day orally; maximum administered dose of 2800 mg in a 70 kg man, with 28 mg absorbed given a bioavailability of 1%). The maximum dose for the present formulation is expected to be about 5 ml twice daily of an 8% sodium cromoglycate formulation. Thus the maximum administered topical daily dose is expected to be 800 mg. Topical bioavailability figures quoted in the literature are from 0.01 to 2.75%. This would mean that the maximum absorbed daily dose is expected to be 0.08 to 22 mg. The systemic dose is therefore expected to be below that achieved by other routes of administration.

Absorption of sodium cromoglycate through the skin may be measured by measuring the presence of sodium cromoglycate in plasma or urine following topical application as described above or as described, for example, in Ishikura et al (1987) cited above or in Ariyanayagam et al (20), as mentioned above.

EXAMPLE 5

Phase II Clinical Trials

Trial 1: a single centre double-blind placebo controlled randomised crossover study using a 4% composition of the invention as described in Example 3 as an adjunct to steroid treatment in children aged 1 to 7 years with atopic dermatitis. Treatment time will be 12 weeks following a 4-week run-in. Evaluation criteria will include any reduction in topical corticosteroid use, SCORAD assessment scores, acceptability of treatment and adverse events.

Subjects are determined to have atopic dermatitis by reference to the diagnostic criteria of Hanifin and Rajika (Hanifin (1982) "Atopic dermatitis" *J Am Acad Dernatol* 6, 1–13). The atopic dermatitis is of moderate to severe grade according to the grading system of Rajika and Langeland (Rajika & Langeland (1989) "Grading of the severity of atopic dermatitis" *Acta Derm Venerol* 144(suppl) 13–14). On entry to the double-blind (treatment) phase, the subjects have a SCORAD score of 25 or more.

The steroid treament is with Betnovate RD™ (betamethasone valerate; a potent corticosteroid). This replaces any corticosteroid treatment previously used by the subject.

Diary cards are completed (by a parent) during the run-in and treatment phases. A urine sample is taken at the end of 12 weeks of test treatment in order to determine the absorption of sodium cromoglycate, as described in Example 4. The severity of itching and sleep disturbance due to atopic dermatitis are recorded twice daily. Global assessments of effectiveness and acceptability of the treatment are also made by the parent.

The order of application of the test lotion and the topical corticosteroid may be specified: for example, the topical corticosteroid may be applied at least 15 minutes after applying the test lotion. The lotion is applied to the affected area of the skin twice daily.

Trial 2: a single centre double-blind placebo controlled randomised crossover study to evaluate the acceptability, tolerability and effects of 3 days pretreatment with 2%, 4% and 8% compositions of the invention on the size of the skin wheal and flare response and itch caused by antigen challenge in volunteer allergic adults.

Kimata and Igarashi (1990) *Allergy* 453, 393–395 and Phillips et al (1996) *Allergy* 51(3), 198–199 have shown that topical sodium cromoglycate inhibits antigen induced wheal and flare reaction in the skin of human subjects. The results of the latter study indicated that a significant effect is observed only after pretreatment (in this case for 3 days) and not after a single dose immediately preceding skin prick testing.

Sodium cromoglycate may have an effect on antigen mediated reactions in the skin of humans and that these effects are relevant to its potential clinical efficacy in conditions such as atopic dermatitis. Any clinical effect is likely to be dependent upon the formulation used achieving good penetration of the skin in order to get to the relevant cells and receptors in the dermis. The demonstration of an inhibitory effect together with a reduction in the associated itching on use of a particular formulation may be supportive of the use of the formulation in paediatric atopic dermatitis and may also provide useful data for the selection of the optimum concentration.

Subjects have a positive skin challenge test response to at least two common allergens, greater than or equal to that of the positive control and at least equal to 10 $mm^2$. Allergens are selected from the following: grass, ragweed tree pollen, cat fur or house dust mite. Subjects undergo skin prick tests with antigens diluted to give mild to moderate wheal responses of 3–5 mm in diameter. Subjects are then allocated to receive in random order each of four treatments (2%, 4%, 8% sodium cromoglycate or placebo), to be applied four times a day for 3 days to one forearm. On day 4, following a final treatment application, subjects are re-challenged with antigen, and the areas of wheal and flare responses and level of itching are assessed after 15 minutes. Treatment periods are separated by washout periods of at least 4 days. Criteria for evaluation are the size of wheal and flare responses to allergen 15 minutes post challenge and the degree of itching at this time as assessed by the VAS scale.

EXAMPLE 6

Phase III Clinical Studies

Two studies are performed as follows:

1)

250 patients with moderate to severe atopy.

Run-in on topical corticosteroid therapy for one month.

Randomised to placebo or active treatment for three months.

Disease modification, measured using standard parameters, and reduction in the amount of corticosteroid used are used to assess treatment efficacy.

A long-term open follow-up is carried out.

2)

250 patients with mild atopy.

Run-in on intermittent topical corticosteroid therapy for one month.

Randomised to placebo or active treatment for three months.

Disease modification, measured using standard parameters, is used to assess treatment efficacy.

A long-term open follow-up is carried out.

Results follow those seen in named patients, as summarised in Example 3. An improvement in symptoms is seen, accompanied by reduced need for corticosteroid treatment. The treatment is well tolerated.

REFERENCES

1. Haider S A. Treatment of atopic eczema in children—. A clinical trial of 10% sodium cromoglycate ointment. *BMJ* (1977); 1570–1572.
2. Thirumoothy T, Greaves M W. Disodium cromoglycate ointment in atopic eczema. *BMJ* (1978); 500–501.
3. Croner S, et al. Sodium cromoglycate ointment in atopic eczema during childhood. *Opuscula Medica* (1981) 26(2): 49–50.
4. Zachafiae H, Thestrup-Pedersen K, Thulin H, Thormann J, Herlin T, Cramers M, Jensen J, Kragballe K, Afzelius H, Overgaard Petersen H. Experimental treatment in atopic dermatitis: immunologial background and preliminary results. *Acta Dermatovener(Stockholm) Suppl.* (1980) 92: 121–127.
5. Haider S A. Treatment of atopic dermatitis in children.— Use of topical sodium cromoglycate. From *The Mast Cell; Its role in Health and Disease.* Eds. Pepys and Edwards (1979); Pitman Medical. 570–6.
6. Pearce C A, Greaves Nff, Plummer V M. Yamamoto S. Effect of sodium cromoglycate on antigen evoked histamine release in human skin. *Clin Exp Immunol* (1974) 17: 437–440.
7. Clegg L S, Church Na, Holgate St. Histamine secretion from humman skin slices induced by anti-IgE and artificial secretagogues and the effects of sodium cromoglycate and salbutamol. *Clin Allergy* (1985) 15(4): 321–328.
8. Okayama Y, Benyon R C, Rees P H, Lowman M A, Hillier K, Church M K. Inhibition profiles of sodium cromoglycate and nedocromil sodium on mediator release from mast cells of human skin, lung, tonsil, adenoid, and intestine. *Clin Exp Allergy* (1992) 22(3): 410–409.
9. Crossman D C, Dashwood N R Taylor G W, Wellings R, Fuller R W. Sodium cromoglycate: evidence of tachykinin antagonist activity in the human skin. *J Appl Physiol* (1993) 75(1): 167–172.
10. Walsh L J. Ultraviolet B irradiation of sin induces mast cell degranulation and release of tumour necrosis factorα. *Immunology and Cell Biology* (1995) 73: 226–233.
11. Page C. Sodium cromoglycate, a tachykinin antagonist. *Lancet* (1994) 343: 70.
12. Edwards A M, Norfis A A. Cromoglycate and asthma. *Lancet* (1994) 343: 426.
13. Ting S, Zweiman B, Lavker R. Cromolyn does not modulate human allergic skin reactions in vivo. *J Allergy Clin Immunol* (1983) 71 (1 Pt 1): 12–17.
14. Van Bever H P, Stevens W J. The effect of local application of disodium cromoglycate (DSCG) solution on skin prick tests. *J Allergy Clin Immunol* (1991) 1: 226A.
15. Grönneberg R, Zetterström O. Effect of disodium cromoglycate on anti-IgE induced early and late skin response in humans. *Clin Allergy* (1985) 15(2) 167–171.
16. Kimata H, Igarashi M. Inhibition of human allergic skin reactions in vivo by pretreatment with cromolyn (disodium cromoglycate). *Allergy* (1990) 45: 393–395.
17. Phillips T J, Kanj L F, Washek D, Lew R. Topical cromolyn can modify human allergic skin reactions. *Allergy* (1996) 51(3) 198–199.
18. Kjellman N-I M and Gustafsson IM. Topical sodium cromoglycate in atopic dermatitis. *Allergy* (1986) 44(6): 423–428.
19. Pike M G and Atherton D J. Failure of a new topical sodium cromoglycate formulation to improve atopic dermatitis. *Eur J Ped* (1988) 148(2): 170.
20. Ariyanayagam M, Barlow T J G, Graham P, Hall-Smith S P, Harris J M. Topical sodium cromoglycate in the management of atopic eczema—a controlled trial. *Br J Dernatol* (1985) 112: 343–348.
21. Neale M G, Brown K, Hodder R W, Auty R M. The pharmacokinetics of sodium cromoglycate in man after intravenous and inhalation adminstration. *Br J Clin Pharmac* (1986) 22: 373–382.
22. Kimata H, Igarashii M I E. Topical cromolyn (disodium cromoglycate) solution in the treatment of young children with atopic dermatitis. *Clin Exp Allergy* (1990) 20: 281–283.
23. Kimata H, Hiratsuka S. Effect of topical sodium cromoglycate solution on atopic dermatitis: combined treatment of sodium cromoglycate solution with the oral antiallergic medication, oxatomide. *Eur J Pediatr* (1994) 153: 66–71.
24. Hiratsuka S, Yoshida A, Ishioka C, Kimata H. Enhancement of in vitro spontaneous IgE production by topical steroids in patients with atopic dermatitis. *J Allergy Clin Immunol* (1996) 98: 107–113.
25. Loh R K S, Jabara H H, Geha R S. Disodium cromoglycate inhibits Sμ→Se deletional switch recombination and IgE synthesis in Human B cells. *J Exp Med* (1994) 180 (2): 663–671.
26. Wu C Y, Sarfati M, Heusser C, Poumier S, Rubio-Trujillo M, Delespesse G. Glucocorticoids increase the synthesis of immunoglobulin E by interleukin-4 stimulated human lymphocytes. *J Clin Invest* (1991) 87: 870–877.
27. McHenery P M, Williams H C, Bingham E A. Management of atopic eczema. *BMJ* (1995) 310: 843–847.
28. Atopic dermatitis and cromolyn. *Clin Exp Allergy* (1990) 20: 243–244.
29. European Task Force on Atopic Dermatitis. Severity scoring of atopic dermatitis: The SCORAD index. *Dermatology* (1993) 186: 23–31.

The invention claimed is:

1. A method for treating a skin condition selected from a group consisting of atopic dermatitis and eczema of a human patient, comprising:
   (a) providing an aqueous and oil phase composition comprising about 1–5% w/v of an amphoteric surfactant, about 0.5–4% w/v of an alkoxylated cetyl alcohol, and about 1–10% w/v of a polar drug selected from the group consisting of sodium cromoglycate and nedocromil sodium; and
   (b) applying said composition to the patient's skin.

2. A method as in claim 1 wherein said alkoxylated cetyl alcohol is selected from the group consisting of polypropoxylated cetyl alcohol and ethoxylated cetyl alcohol.

3. A method according to claim 1 wherein the amphoteric surfactant is a balanced amphoteric surfactant.

4. A method according to claim 1 wherein the amphoteric surfactant comprises disodium cocoamphodiacetate.

5. A method according to claim 1 wherein the composition further comprises a corticosteroid.

6. A method according to claim 1 wherein the composition is an oil-in-water emulsion.

7. A method according to claim 1 wherein the composition is a foam.

8. A composition consisting essentially of:

sorbitan tristearate or non-ionic emulsifying wax 0.5 to 5% w/v

| | |
|---|---|
| glycerol monostearate | 0.5 to 5% w/v |
| light liquid paraffin | 1 to 20% w/v |
| white soft paraffin | 1 to 10% w/v |
| iso propyl myristate | 0.5 to 5% w/v |
| polar drug | 0.1 to 20% w/v |

-continued

| | |
|---|---|
| disodium edetate | 0.01 to 1% w/v |
| amphoteric surfactant | 0.1 to 10% w/v |
| alkoxylated cetyl alcohol | 0.1 to 10% w/v |
| triclosan | 0.01 to 1% w/v |
| benzyl alcohol | 0.01 to 1% w/v |
| purified water | to 100% of the emulsion. |

9. A method as in claim 1 wherein said composition is packaged in a tube, tub, bottle or pressurised aerosol container.

* * * * *